US010492864B2

(12) United States Patent
Zerfas et al.

(10) Patent No.: US 10,492,864 B2
(45) Date of Patent: Dec. 3, 2019

(54) METHODS AND APPARATUS RELATED TO A DISTAL END PORTION OF AN OPTICAL FIBER HAVING A SUBSTANTIALLY SPHERICAL SHAPE

(71) Applicant: Boston Scientific Scimed, Inc., Maple Grove, MN (US)

(72) Inventors: Jeffrey W. Zerfas, Bloomington, IN (US); Carl Donadio, Grafton, MA (US); David W. Robertson, Framingham, MA (US); Richard Tumminelli, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 266 days.

(21) Appl. No.: 15/417,027

(22) Filed: Jan. 26, 2017

(65) Prior Publication Data

US 2017/0135767 A1 May 18, 2017

Related U.S. Application Data

(63) Continuation of application No. 12/948,941, filed on Nov. 18, 2010, now abandoned.

(Continued)

(51) Int. Cl.
*A61B 18/26* (2006.01)
*A61B 18/24* (2006.01)

(Continued)

(52) U.S. Cl.
CPC ............ *A61B 18/26* (2013.01); *A61B 18/245* (2013.01); *G02B 6/0008* (2013.01);

(Continued)

(58) Field of Classification Search
CPC ............ A61B 18/26; A61B 2018/2266; G02B 6/03638; G02B 6/02395; G02B 6/2552; G02B 6/262

(Continued)

(56) References Cited

U.S. PATENT DOCUMENTS 4,641,912 A 2/1987 Goldenberg
4,648,892 A 3/1987 Kittrell et al.

(Continued)

FOREIGN PATENT DOCUMENTS

CN 101230972 A 7/2008
EP 0355200 A1 2/1990

(Continued)

OTHER PUBLICATIONS

PCT International Search Report and PCT Written Opinion of the International Searching Authority, for PCT/US2010/057152, dated Feb. 24, 2011 (9 pages).

*Primary Examiner* — Nathan J Jenness
(74) *Attorney, Agent, or Firm* — Bookoff McAndrews, PLLC

(57) ABSTRACT

An apparatus includes an optical fiber extending from a proximal end to a distal end. The optical fiber may include a cladding layer circumferentially disposed about a core layer and a substantially spherically shaped portion at the distal end. The apparatus may also include a first coating circumferentially disposed on a first length of the cladding layer, and a second coating circumferentially disposed on a second length of the cladding layer. The second length may extend distally from a region proximate the distal end of the first coating.

20 Claims, 7 Drawing Sheets

Related U.S. Application Data

(60) Provisional application No. 61/262,395, filed on Nov. 18, 2009.

(51) Int. Cl.

| | |
|---|---|
| ***G02B 6/02*** | (2006.01) |
| ***G02B 6/036*** | (2006.01) |
| ***A61B 18/22*** | (2006.01) |
| ***G02B 6/25*** | (2006.01) |
| ***G02B 6/255*** | (2006.01) |
| ***G02B 6/26*** | (2006.01) |
| ***F21V 8/00*** | (2006.01) |

(52) U.S. Cl.

CPC ..... *G02B 6/02395* (2013.01); *G02B 6/03638* (2013.01); *G02B 6/25* (2013.01); *G02B 6/2552* (2013.01); *G02B 6/262* (2013.01); *A61B 2018/2222* (2013.01); *A61B 2018/2266* (2013.01)

(58) Field of Classification Search

USPC ...................................................... 606/15–16

See application file for complete search history.

(56) References Cited

U.S. PATENT DOCUMENTS

| | | | |
|---|---|---|---|
| 4,693,556 | A | 9/1987 | McCaughan, Jr. |
| 4,695,697 | A | 9/1987 | Kosa |
| 5,133,709 | A | 7/1992 | Prince |
| 5,242,437 | A | 9/1993 | Everett et al. |
| 5,897,551 | A | 4/1999 | Everett et al. |
| 5,925,033 | A | 7/1999 | Aita et al. |
| 6,966,902 | B2 | 11/2005 | Brown |
| 2005/0147735 | A1* | 7/2005 | Lowery .................. A61L 27/34 427/2.1 |
| 2008/0177257 | A1 | 7/2008 | Smith et al. |

FOREIGN PATENT DOCUMENTS

| | | |
|---|---|---|
| JP | H 0255053 A | 2/1990 |
| JP | H 04-276706 | 10/1992 |
| JP | 09-318825 | 12/1997 |
| JP | 2001-021772 A | 1/2001 |
| JP | 2002-082236 | 3/2002 |
| JP | 2004-205970 | 7/2004 |
| JP | 2005-010242 | 1/2005 |
| JP | 2005-115020 | 4/2005 |
| JP | 2005-156831 | 6/2005 |
| JP | 2005-208025 | 8/2005 |
| JP | 2006-515682 | 6/2006 |
| WO | WO 2004/048285 | 6/2004 |

* cited by examiner

METHODS AND APPARATUS RELATED TO A DISTAL END PORTION OF AN OPTICAL FIBER HAVING A SUBSTANTIALLY SPHERICAL SHAPE

The present application is related to, and claims priority from, U.S. Provisional Patent Application Ser. No. 61/262,395 filed on Nov. 18, 2009 which is incorporated herein by reference in its entirety.

BACKGROUND

Embodiments relate generally to medical devices, and, in particular, to a distal end portion of an optical fiber that has a substantially spherical shape.

During a ureteroscopy procedure, a medical practitioner can insert an endoscope (also can be referred to as a ureteroscope) into a patient's urinary tract, for example, over a guide wire to locate an undesirable object such as a kidney stone or a bladder stone. Once the stone is located, an optical fiber can be introduced into a working channel of the endoscope and advanced within the working channel until the optical fiber comes into contact with or in close proximity to the stone. Electromagnetic radiation from, for example, a holmium (Ho) laser can be directed through the optical fiber towards the stone to break the stone into fragments. The fragments can be removed with a basket tool via the working channel or flushed through normal urinary activity. This type of ureteroscopy procedure, which can be minimally invasive, can be performed under, for example, a general anesthetic.

Many known optical fibers that are used in ureteroscopy procedures have cleaved distal ends with edges that can be relatively sharp. The distal end edge(s) of a known optical fiber can snag on and/or cut into an inner surface (e.g., an inner liner) of a working channel of an endoscope as the optical fiber is advanced within the working channel during a ureteroscopy procedure. In some instances, for example, a snag can result in an undesirable delay during a ureteroscopy procedure and/or in damage (e.g., irreparable harm) to the endoscope. The potential for the distal end of a known optical fiber to snag or cut a working channel of an endoscope is particularly high when the optical fiber is advanced through a portion of the working, channel that is intentionally or accidentally bent during a ureteroscopy procedure. Thus, a need exists for a distal end portion of an optical fiber that can address at least some of these issues.

SUMMARY

In one embodiment, an apparatus is disclosed. The apparatus may include an optical fiber extending from a proximal end to a distal end. The optical fiber may include a cladding layer circumferentially disposed about a core layer and a substantially spherically shaped portion at the distal end. The apparatus may also include a first coating circumferentially disposed on a first length of the cladding layer, and a second coating circumferentially disposed on a second length of the cladding layer. The second length may extend distally from a region proximate the distal end of the first coating.

Various embodiments of the apparatus may also include the second length extending from the distal end of the first length to a proximal end of the substantially spherically shaped portion; the second length extending from a region proximal to the distal end of the first length to a region distal to a proximal end of the substantially spherically shaped portion; a distal end of the second length may be proximal to a distal end of the substantially spherically shaped portion; an index of refraction of the first coating may be substantially equal to an index of refraction of the second coating; an index of refraction of the first coating may be different from the index of refraction of the second coating; the first coating may include a first inner coating and a first outer coating, wherein the first inner coating is positioned radially inwards of the first outer coating; the second coating may include a second inner coating and a second outer coating, wherein the second inner coating is positioned radially inwards of the second outer coating; a diameter of the substantially spherically shaped portion may be greater than a diameter of the cladding layer; the apparatus may further include a recessed portion positioned between a distal end of the second length and a proximal end of the substantially spherically shaped portion, the recessed portion may have an outer diameter smaller than an outer diameter of each of a portion distal to the recessed portion and a portion proximal to the recessed portion.

In another embodiment, a method of fabricating a medical device is disclosed. The method may include removing a portion of a first coating at a distal end portion of an optical fiber such that an exposed portion of the optical fiber is exposed. The method may also include heating at least a first portion of the exposed portion to transform the first portion to a substantially spherically shaped portion of the exposed portion, and disposing a second coating on at least a second portion of the exposed portion after the heating.

Various embodiments of the method may also include disposing the second coating between a distal end of the first coating and a proximal end of the substantially spherically shaped portion; applying the second coating such that the substantially spherically shaped portion and a distal region of the first coating are coated; the heating may include melting the first portion and allowing surface tension to transform the molten first portion to the substantially spherically shaped portion; the method may further include applying a laser through the optical fiber to remove a portion of the second coating at a distal end of the substantially spherically shaped portion.

In another embodiment, a fiber optic medical device is disclosed. The device may include a core extending from a proximal end to a distal end and a cladding layer circumferentially disposed about the core and extending from the proximal end to the distal end. The device may also include a covering layer circumferentially disposed about the cladding layer extending from the proximal end to a first end proximal to the distal end, and a substantially spherical optical component integral with the core and the cladding layer positioned at the distal end. The device may further include a coating circumferentially disposed about a region extending from proximate the first end towards the optical component.

Various embodiments of the device may also include a proximal end of the coating overlapping a distal end of the covering, and a distal end of the coating positioned between a proximal end and a distal end of the optical component; the coating may include an inner coating and an outer coating positioned radially outwards of the inner coating; a diameter of the substantially spherical optical component may be greater than a diameter of the cladding layer.

In one embodiment, an apparatus includes an optical fiber that has a cladding layer and a distal end portion. The distal end portion of the optical fiber has a substantially spherical shape. The apparatus also includes a first axial coating disposed on at least a portion of the cladding layer of the optical fiber and a second axial coating disposed on at least a portion of the cladding layer and between the first axial coating and the distal end portion. The second axial coating can be different than the first axial coating.

In some embodiments, an index of refraction of the first axial coating can be substantially equal to an index of refraction of the second axial coating. In some embodiments, an index of refraction of the first axial coating can be different than an index of refraction of the second axial coating. In some embodiments, a volume of the distal end portion can be defined such that a beam profile associated with laser energy propagated along the optical fiber and out of a distal surface of the distal end portion can be substantially unchanged at an interface defined by the distal surface of the distal end portion.

In some embodiments, a diameter of the distal end portion can be greater than a diameter of the cladding layer of the optical fiber. In some embodiments, the cladding layer can have a fluorine concentration and the distal end portion can have a fluorine concentration.

In some embodiments, a method can include removing a portion of a first axial coating disposed on a distal end portion of an optical fiber such that a first portion of the optical fiber and a second portion of the optical fiber are exposed. At least the first portion of the optical fiber can be heated such that the first portion of the distal end portion forms a spherical shape. A second axial coating on the second portion of the optical fiber can be disposed after the heating. The second portion of the optical fiber being mutually exclusive from the first portion of the optical fiber.

In some embodiments, the disposing can include disposing the second axial coating between the first axial coating and the distal end portion. In some embodiments, the disposing can include disposing on a portion of a cladding layer of the optical fiber and between the first axial coating and the distal end portion. In some embodiments, the heating can include heating such that a diameter of the distal end portion is greater than a diameter of the second axial coating.

In some embodiments, the first axial coating can be removed from a cladding layer of the optical fiber. The first axial coating can have an index of refraction lower than an index of refraction of the cladding layer. In some embodiments, the second axial coating can have an index of refraction lower than the index of refraction of a cladding layer of the optical fiber. In some embodiments, the first axial coating can be an acrylate coating. The second axial coating can be an acrylate coating.

In another embodiment, a method can include heating at a first time a distal end portion of the optical fiber within a heating zone associated with a heating element such that a substantially spherical portion can be formed from the distal end portion of the optical fiber. The distal end portion can be moved along a longitudinal axis of the optical fiber at a second time. At a third time the distal end portion of the optical fiber can be heated such that a volume of the spherical portion at the third time is greater than a volume of the spherical portion at the first time.

In some embodiments, the moving can include moving in a distal direction. In some embodiments, the heating element can be an electrode associated with a fusion splicer. In some embodiments, at least a portion of the spherical portion can be formed from a cladding layer associated with the distal end portion of the optical fiber.

In some embodiments, the method can also include removing at least one layer of the distal end portion of the optical fiber disposed outside of a core portion of the distal end portion of the optical fiber before the heating at the first time. In some embodiments, the method can also include disposing an optical layer on a cladding layer of the optical fiber after the heating at the third time. The optical layer can have an index of refraction lower than an index of refraction associated with a core portion of the optical fiber.

In some embodiments, the method can also include disposing an optical layer on a cladding layer of the optical fiber after the heating at the second time, the optical layer can be in contact with a proximal side wall of the spherical portion. In some embodiments, the method can also include removing a first layer from the distal end of the optical fiber before the heating at the first time. The first layer can have an index of refraction lower than an index of refraction associated with the optical fiber. A second layer on the optical fiber can be disposed after the heating at the second time. The second layer can have an index of refraction substantially equal to the index of refraction of the first layer.

In another embodiment, an apparatus an optical fiber can be associated with an endoscope. The apparatus can also include an optical component that can have a substantially spherical shape coupled to a distal portion of the optical fiber. A volume of the optical component can be defined such that a first portion of a beam profile associated with the optical fiber and the optical component can have a focal length substantially the same as a focal length of a second portion of the beam profile distal to and outside of the distal end portion. The first portion of the beam profile can have a beam width substantially equal to abeam width of the second portion of the beam profile.

In some embodiments, the beam width of the first portion of the beam profile can be substantially equal to a diameter of a core of the optical fiber. In some embodiments, the beam profile can be substantially uniform. In some embodiments, laser energy transmitted from the proximal end of the optical fiber can define the beam profile. The volume of the distal end portion can be defined such that a circumferential portion of the laser energy is substantially unrefracted at an interface defined by a distal surface of the distal end portion.

In some embodiments, a diameter of the distal end portion can be greater than a diameter of the optical fiber. In some embodiments, the optical fiber can have a fluorinated cladding layer disposed outside of a core portion of the optical fiber. In some embodiments, the distal end portion can have a fluorine concentration. In some embodiments, the optical fiber can have a silica core.

In another embodiment, an apparatus can include an optical fiber having a distal end portion, a first axial portion, and a second axial portion disposed between the first axial portion and the distal end portion. The distal end portion can have a substantially spherical shape. The apparatus can also include a core of the second axial portion that has an outer-diameter less than an outer-diameter of a core of the first axial portion of the optical fiber and less than an outer-diameter of the distal end portion.

In some embodiments, the outer-diameter of the distal end portion can be greater than the outer-diameter of the core portion of the first axial portion of the optical fiber. The apparatus of claim can also include a cladding layer disposed on the first axial portion of the optical fiber. In some embodiments, the apparatus can also include a cladding layer disposed on the first axial portion of the optical fiber. The second axial portion of the optical fiber member can define a recess disposed between a distal end of the cladding layer and a proximal surface of the distal end portion.

In some embodiments, the second axial portion can have a concave portion. In some embodiments, the apparatus can also include a cladding layer disposed on the concave portion of the second axial portion. In some embodiments, the optical fiber can be a silica-based optical fiber associated with an endoscope. In some embodiments, the distal end portion can be formed from a distal end portion of the optical fiber.

DETAILED DESCRIPTION

Figure 1:
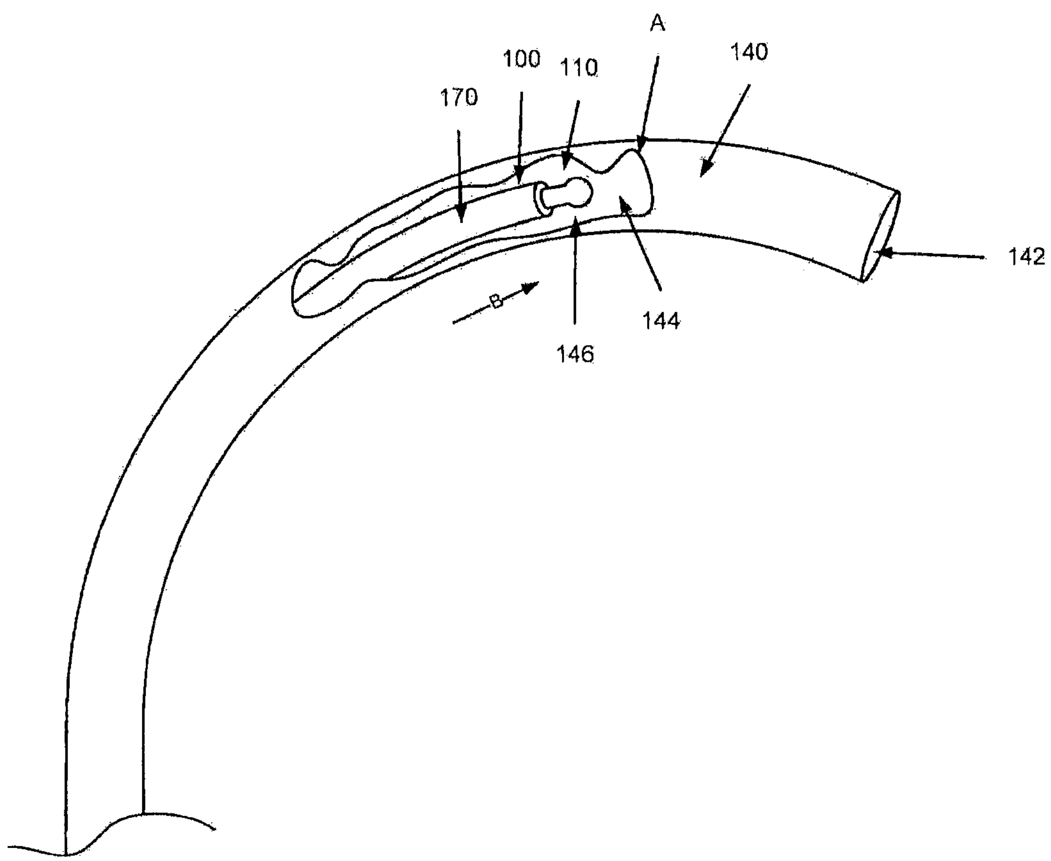
FIG. 1 is a schematic diagram that illustrates a side view of a distal end portion of an optical fiber disposed within a lumen defined by an endoscopic tube, according to an embodiment.

The devices and methods described herein are generally related to an optical fiber configured to treat a target treatment area within a body of a patient. Specifically, the optical fiber can be used to transmit laser energy from a laser source to the target treatment area when the optical fiber is disposed within an endoscope. One end of the optical fiber, the proximal end portion, can be coupled to the laser source while the other end of the optical fiber, the distal end portion, can be inserted into the patient's body to provide the laser treatment. The optical fiber can include, for example, a fiber core, one or more cladding layers disposed around the fiber core, a buffer layer disposed around the cladding layer(s), and a jacket layer (disposed around the buffer layer). In some embodiments, the buffer layer can be referred to as a cladding layer. The jacket layer can also be referred to as a jacket or as a jacket coating, and the buffer layer can be referred to as a buffer coating.

A distal end portion of the optical fiber can have a substantially spherical shape. In some embodiments, the substantially spherical shape at the distal end portion of the optical fiber also can be referred to as an optical component. In some embodiments, the distal end portion of the optical fiber can be heated using a heating source (e.g., a fusion splicer) until a desirable substantially spherical shape is formed. In some embodiments, an outer diameter of the distal end portion of the optical fiber can be greater than an outer diameter of another portion of the optical fiber (e.g., a cladding layer of the optical fiber).

In some embodiments, the optical fiber can include a first axial coating disposed on at least a portion of a cladding layer of the optical fiber and a second axial coating disposed on at least a portion of the cladding layer. An axial coating can be a coating circumferentially around at least a portion of an optical fiber. The second axial coating can be disposed between the first axial coating and the distal end portion after the distal end portion has been formed into a substantially spherical shape. In some embodiments, the second axial coating can have substantially the same properties as or different properties than the first axial coating. In some embodiments, a volume of the distal end portion can be defined so that an optical path associated with laser energy propagated along the optical fiber and out of a distal surface of the distal end portion can be substantially unrefracted at an interface defined by the distal surface of the distal end portion of the optical fiber.

In some embodiments, the devices and methods described herein can be used in treating symptoms related to, for example, a kidney stone and/or an enlarged prostate gland, a condition known as Benign Prostatic Hyperplasia (BPH). Specifically, laser energy from a holmium.YAG (Ho:YAG) laser can be propagated through the optical fiber to remove the kidney stone and/or the obstructive prostate tissue. The Ho:YAG surgical laser is a solid-state, pulsed laser that emits light at a wavelength of approximately 2100 nanometers (nm). This wavelength of light is particularly useful for, for example, tissue ablation because it is strongly absorbed by water. An advantage of Ho.YAG lasers is that they can be used for both tissue cutting and for coagulation.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a nurse, a technician, etc.) who would insert a medical device into a patient. Thus, for example, an optical fiber end inserted inside a patient's body would be the distal end of the optical fiber, while the optical fiber end outside of a patient's body would be the proximal end of the optical fiber.

FIG. 1 is a schematic diagram that illustrates a side view of a distal end portion 110 of an optical fiber 100 disposed within a lumen 144 defined by an endoscopic tube 140, according to an embodiment. As shown in FIG. 1 through cut-away A in the endoscopic tube 140, the distal end portion 110 of the optical fiber 100 has a substantially spherical shape. Because the distal end portion 110 of the optical fiber 100 has a substantially spherical shape, the distal end portion 110 of the optical fiber 100 can be moved (e.g., advanced), for example, in a distal direction B within the lumen 144 without snagging on an inner surface 146 that defines the lumen 144 of the endoscopic tube 140. Specifically, a smooth distal end surface of the distal end portion 110 can slide along the inner surface 146 of the endoscopic tube 140 when the distal end portion 110 of the optical fiber 100 is moved. In some embodiments, the inner surface can be associated with an integral inner liner or a separate inner liner.

The optical fiber 100 has a fiber core that is disposed within and substantially along an entire length of the optical fiber 100 including the spherical-shaped distal end portion 100. Proximal to the distal end portion 110 of the optical fiber 100, the optical fiber 100 has an outer layer 170 that is disposed outside of the fiber core and can include, for example, one or more jacket layers, one or more buffer layers (which can function as a cladding layer or the only cladding layer), and/or one or more cladding layers (not shown in FIG. 1). In some embodiments, the jacket layer(s) (e.g., a polymer-based layer), the cladding layer(s) and/or the buffer layer(s) are also disposed around at least a portion of the distal end portion 110 of the optical fiber 100. In some embodiments, the spherical-shaped distal end portion 110 can be made from material associated with the fiber core, or the fiber core and one or more cladding layers. In other words, the spherical-shaped distal end portion 100 can be made from a portion of the fiber core, or a mixture of a portion of the fiber core and a portion of one or more cladding layers.

In some embodiments, the optical fiber 100 can be a silica-based optical fiber. For example, the fiber core can be a pure silica fiber, and a cladding layer disposed around the fiber core can be a doped-silica cladding layer. In some embodiments, the cladding layer(s) of the optical fiber 100 can be doped with a dopant (e.g., a fluorine dopant, a chlorine dopant, a rare-earth dopant, a germanium dopant, an alkali-metal dopant, an alkali-metal-oxide dopant, etc.). The cladding layer can be a single cladding or a double cladding that can be made of a hard polymer or a silica. The buffer layer (which can function as a cladding layer) can be made of a hard polymer or acrylate, for example. When the outer layer 170 of the optical fiber 100 includes a jacket layer, the jacket layer can be made of Tefzel®, for example, or can be made of other polymer-based substances.

In some embodiments, the fiber core can be made of a suitable material for the transmission of laser energy from a laser source (not shown). In some embodiments, for example, the fiber core can be made of silica with a low hydroxyl ($OH^-$) ion residual concentration. Laser energy wavelengths ranging from about 500 nm to about 2100 nm can be propagated within the fiber core of the optical fiber 100 during a surgical procedure. An example of low hydroxyl (low-OH) fibers used in medical devices is described in U.S. Pat. No. 7,169,140 to Kume, the disclosure of which is incorporated herein by reference in its entirety. The fiber core can be a multi-mode fiber core and can have a step or graded index profile. The fiber core can also be doped with a dopant (e.g., an amplifying dopant). In some embodiments, laser energy can be transmitted into (e.g., launched into) the fiber core from a laser source via a connector (e.g., a launch connector) such as that described in U.S. patent application Ser. No. 12/340,350, filed Dec. 19, 2008, entitled "Methods and Apparatus Related to a Launch Connector Portion of a Ureteroscope Laser-Energy-Delivery Device," which is incorporated by reference herein in its entirety.

The lumen 144 of the endoscopic tube 140 can also be configured to receive various medical devices or tools, such as, for example, irrigation and/or suction devices, forceps, drills, snares, needles, etc. In some embodiments, the endoscopic tube 140 can define one or more lumens, in addition to lumen 144, through which one or more medical devices can be received. An example of such an endoscopic tube 140 with Multiple lumens is described in U.S. Pat. No. 6,296,608 to Daniels et al., the disclosure of which is incorporated herein by reference in its entirety. In some embodiments, a fluid channel (not shown) can be defined by the endoscopic tube 140 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscopic tube 140, for example, and coupled to a proximal end portion of an optical fiber (not shown) that can be disposed within a lumen (e.g., lumen 144) of the endoscopic tube 140. Such an embodiment can allow a medical practitioner to view the interior of a patient's body through the eyepiece.

FIGS. 2A through 2E, are schematic diagrams that illustrate a method for producing a distal end portion 210 that has a substantially spherical shape, according to an embodiment. The distal end portion 210 is heated using a heating source 28 until the distal end portion 210 softens (e.g., flows) and the substantially spherical shape is formed. The substantially spherical shape can be defined by surface tension forces associated with the softened material of the distal end portion 210. The heating source 28 can be, for example, a carbon dioxide ($CO_2$) laser source, an electric arcing source, and/or a gas heating source. The heating source 28 can be included in, for example, a fusion splicer. The heating source 28 can have one or more elements (e.g., arcing elements, electrical heating elements) that can be disposed around different sides of the distal end portion 210 (i.e., disposed at least two different locations about the perimeter of the distal end portion 210).

Figure 2A:
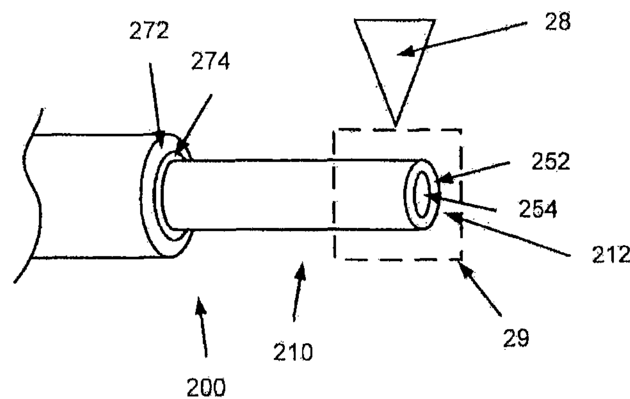
FIG. 2A is a schematic diagram that illustrates a perspective view of a distal end portion of an optical fiber disposed within a heating zone of a heat source, according to an embodiment.

FIG. 2A is a schematic diagram that illustrates a perspective view of a distal end portion 210 of an optical fiber 200 disposed within a heating zone 29 of the heat source 28, according to an embodiment. Specifically, a cleaved distal end 212 of the distal end portion 210 is disposed within the heating zone 29 associated with a heating source 28. The cleaved distal end 212 can be defined using, for example, a scoring and breaking method and/or a cutting instrument. In some embodiments, the cleaved distal end 212 can be substantially flat and/or polished. The distal end portion 210 of the optical fiber 200 can be mutually exclusive from other portions of the optical fiber 200 disposed outside of the distal end portion 210 of the optical fiber 200.

As shown in FIG. 2A, the optical fiber has a fiber core 254 (e.g., a substantially pure silica fiber core) and a cladding layer 252 (e.g., a fluorine-doped cladding layer) disposed circumferentially around the fiber core 254. Proximal to the cleaved distal end 212 of the distal end portion 210, a buffer layer 274 (e.g., an acrylate layer) and a jacket layer 272 (e.g., a jacket layer made of a polymer-based material) are disposed around the cladding layer 252. A portion of the buffer layer 274 and the jacket layer 272 has been stripped from the distal end portion 210 to expose the cladding layer 252 (as shown in FIG. 2A) of the distal end portion 210 of the optical fiber 100. In some embodiments, the cladding layer 252 can be chemically and/or mechanically stripped exposing at least a portion of the fiber core 254.

As the cleaved distal end 212 of the distal end portion 210 is heated (e.g., heated during a heating cycle) and changes into the substantially spherical shape, a length of the distal end portion 210 can decrease. Specifically, material from the distal end portion 210 is changed from a cylindrical shape into the substantially spherical shape. The cleaved distal end 212 of the distal end portion 210 can be placed within a distal portion of the heating zone 29, as shown in FIG. 2A, so that a duration with which at least a portion of the distal end portion 210 is heated within the heating source 28 can be increased despite the shortening of the distal end portion 210.

Figure 2B:
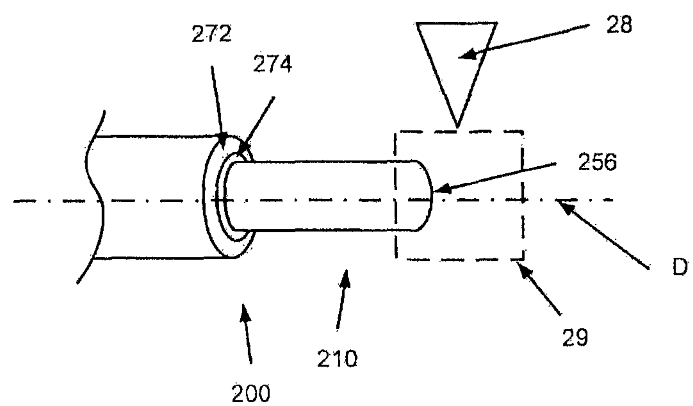
FIG. 2B is a schematic diagram that illustrates a perspective view of a distal end portion of an optical fiber after being heated during a first heating cycle, according to an embodiment.

FIG. 2B is a schematic diagram that illustrates a perspective view of the distal end portion 210 of the optical fiber 200 after being heated during a first heating cycle discussed with respect to FIG. 2A, according to an embodiment. As shown in FIG. 2B, the distal end portion 210 of the optical fiber 200 has formed into a rounded shape 256 in response to heat applied by the heating source 28. Also as shown in FIG. 2B, the distal end portion 210 of the optical fiber 200 has decreased in length (compared with that shown in FIG. 2A).

In some embodiments, the distal end portion 210 of the optical fiber 200 can be heated during the first heating cycle (e.g., a single heating cycle) until the distal end portion 210 has a specified shape and/or a specified length. In some embodiments, the first heating cycle can be defined based on one or more parameter values such as a temperature and/or a duration defined based on, for example, theoretical data and/or empirical data. In some embodiments, the theoretical data and/or empirical data can be related to a fiber characteristic such as an optical fiber size, an optical fiber thermal property, an optical fiber material property, and so forth.

Figure 2C:
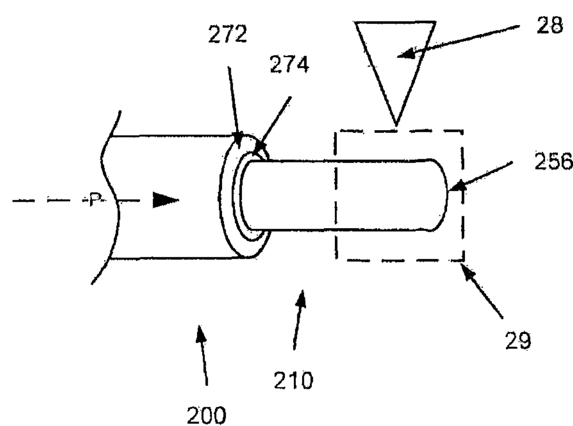
FIG. 2C is a schematic diagram that illustrates a perspective view of a distal end portion of an optical fiber after at least a portion of the distal end portion is moved distally within a heating zone, according to an embodiment.

FIG. 2C is a schematic diagram that illustrates a perspective view of the distal end portion 210 of the optical fiber 200 after at least a portion of the distal end portion 210 is moved distally (shown as direction P) within the heating zone 29, according to an embodiment. The distal end portion 210 of the optical fiber 200 can be moved after the first heating cycle discussed in connection with FIG. 2B has been completed.

Figure 2D:
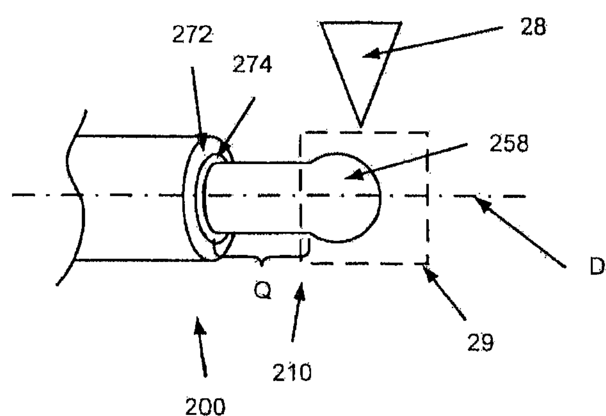
FIG. 2D is a schematic diagram that illustrates a perspective view of a distal end portion of an optical fiber after being heated during a second heating cycle, according to an embodiment.

FIG. 2D is a schematic diagram that illustrates a perspective view of the distal end portion 210 of the optical fiber 200 after being heated during a second heating cycle, according to an embodiment. The second heating cycle can be performed after the distal end portion 210 of the optical fiber 200 is moved distally as discussed in connection with FIG. 2C. As shown in FIG. 2D, the distal end portion 210 of the optical fiber 200 has a substantially spherical shaped portion 258 formed during the second heating cycle. Although any size of spherical portion may be formed, in some embodiments, the substantially spherical shaped portion 258 may have a diameter between about 300 microns to about 600 microns. As shown in FIG. 2D, a portion Q of the cladding layer 252 of the optical fiber 200 remains exposed after the substantially spherical shaped portion 258 is formed (and after the second heating cycle). The portion Q can be referred to as a remaining exposed portion Q. In some embodiments, if the cladding layer 252 has been previously stripped, the remaining exposed portion Q can be the outer surface of the fiber core 254.

The substantially spherical shaped portion 258 has a volume of material that is substantially made from the material of the distal end portion 210 of the optical fiber 200 (e.g., the fiber core 252, the cladding layer 254). In some embodiments, relatively small amounts of material of the distal end portion 210 are removed (e.g., burned, sublimed) during the first heating cycle and/or the second heating cycle.

Similar to the first heating cycle, the distal end portion 210 of the optical fiber 200 can be heated during the second heating cycle until the distal end portion 210 has a specified shape (e.g., a specified volume of the substantially spherical shaped portion 258) and/or a specified length. In some embodiments, the second heating cycle can be defined based on one or more parameter values such as a temperature (e.g., a temperature greater than 1300° F.) and/or a duration (e.g., a time period shorter than 1 second, a time period longer than 1 second, a time period lasting several minutes) defined based on, for example, theoretical data and/or empirical data. In some embodiments, the temperature can be determined based on a power setting (e.g., a wattage setting, a power setting of approximately 20 milliamps) of the heating source 28. In some embodiments, the theoretical data and/or empirical data can be related to a fiber characteristic such as an optical fiber size, an optical fiber thermal property, an optical fiber material property, and so forth. In some embodiments, the parameter value(s) that can be used to define the second heating can be different than the parameter value(s) used to define the first heating cycle. In some embodiments, the distal end portion 210 of the optical fiber 200 can be rotated about a longitudinal axis D (or centerline) of the distal end portion 210 of the optical fiber 200 while the distal end portion 210 is being heated by the heating source 28 within the heating zone 29 during the first heating cycle and/or the second heating cycle.

In some embodiments, the distal end portion 210 of the optical fiber 200 can be moved one or more times (e.g., rotated, moved in a proximal direction, moved in a distal direction) before, after, and/or during one or more heating cycles until the distal end portion 210 has a desirable spherical (or substantially spherical) shape. The movements can be continuous, periodic, or random. For example, a distal end portion of an optical fiber can be moved (e.g., gradually moved) continuously in a distal direction and/or rotated within a heating zone until a desirable spherical (or substantially spherical) shape is formed. In some embodiments, for example, a distal end portion of an optical fiber can be moved only during two heating cycles and not moved between the two heating cycles. The time period between heating cycles can be a specified duration (e.g., a time period shorter than 1 second, a time period longer than 1 second, a time period lasting several minutes).

Although two heating cycles are described as being used to form the substantially spherically shaped portion 258, in some embodiments, a different number of heating cycles may be used. For instance, in an embodiment that uses only one heating cycle, the substantially spherically shaped portion 258 may be formed by heating the distal end portion 210 in one heating cycle for a predetermined amount of time, such as, for example, about 5 seconds. In some embodiments, one or more of the heating cycle(s) (e.g., the first heating cycle, the second heating cycle) can be modified dynamically using, for example, a feedback control loop and/or a feed-forward control loop. For example, a temperature within the first heating cycle can be modified (e.g., gradually increased) during the first heating cycle based on a shape of the distal end portion 210 of the optical fiber 200. In some embodiments, the heating cycle(s) and/or the movement(s) can be defined based on, for example, a property (e.g., a size, a material type, an electrical property) of the distal end portion 210 of the optical fiber 200. In some embodiments, a method for producing the substantially spherical shape at the distal end portion 210 of the optical fiber 200 can include a cooling cycle, for example, to plastically set the distal end portion 210 of the optical fiber 200 after, for example, the first heating cycle.

Figure 2E:
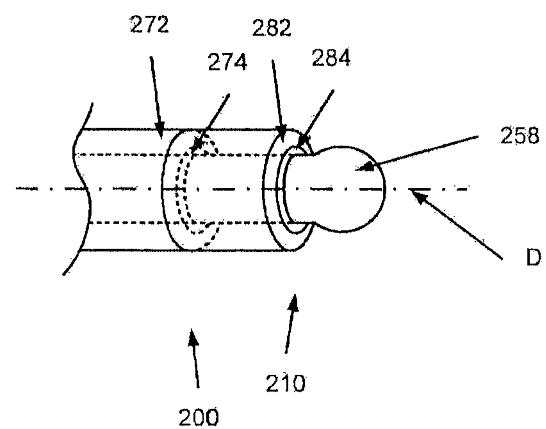
FIG. 2E is a schematic diagram that illustrates a perspective view of a distal end portion of an optical fiber after a spherical shape has been formed at the distal end portion of the optical fiber, according to an embodiment.

FIG. 2E is a schematic diagram that illustrates a perspective view of the distal end portion 210 of the optical fiber 200 after the substantially spherical shaped portion 258 has been formed at the distal end portion 210 of the optical fiber 200, according to an embodiment. As shown in FIG. 2E, a buffer layer 284 is disposed between the buffer layer 274 and the substantially spherical shaped portion 258 at the distal end portion 210 of the optical fiber 200. Also a jacket layer 282 is disposed between the jacket layer 274 (shown in dashed lines) and the substantially spherical shaped portion 258 at the distal end portion 210 of the optical fiber 200. The buffer layer 284 and the jacket layer 282 can be disposed circumferentially around the longitudinal axis D (or centerline) of the distal end portion 210 of the optical fiber 200 to, for example, cover the remaining exposed portion Q, for example, so that it can be protected. The buffer layer 284 and the jacket layer 282 can be disposed circumferentially around the longitudinal axis D (or centerline) of the distal end portion 210 of the optical fiber 200 to, for example, prevent laser energy propagating through the optical fiber 200 from being transmitted out of the cladding layer 252 (e.g., the remaining exposed portion Q) of the optical fiber 200.

In some alternative embodiments, only the buffer layer 284 or only the jacket layer 282 is disposed around the remaining exposed portion Q of the optical fiber 200 after the substantially spherical shaped portion 258 has been formed. The buffer layer 284 and/or the jacket layer 282 can be disposed around the remaining exposed portion Q of the optical fiber 200 using a deposition process. In some embodiments, the buffer layer 284 can have a different index of refraction and/or thickness than the buffer layer 274. In some embodiments, the buffer layer 284 can be made of a different material the buffer layer 274. In some embodiments, the jacket layer 282 can have a different index of refraction and/or thickness than the jacket layer 272. In some embodiments, the jacket layer 282 can be made of a different material than the jacket layer 272.

In some embodiments, one or more buffer layers and/or one or more jacket layers can be at least partially disposed around the remaining exposed portion Q of the optical fiber 200 after the substantially spherical shaped portion 258 has been formed. In some embodiments, the jacket layer 282 and/or the buffer layer 284 can collectively be referred to as a coating segment (e.g., a first coating segment) that is different than a coating segment (e.g., a second coating segment) associated with the jacket layer 272 and/or the buffer layer 274.

Figure 3:
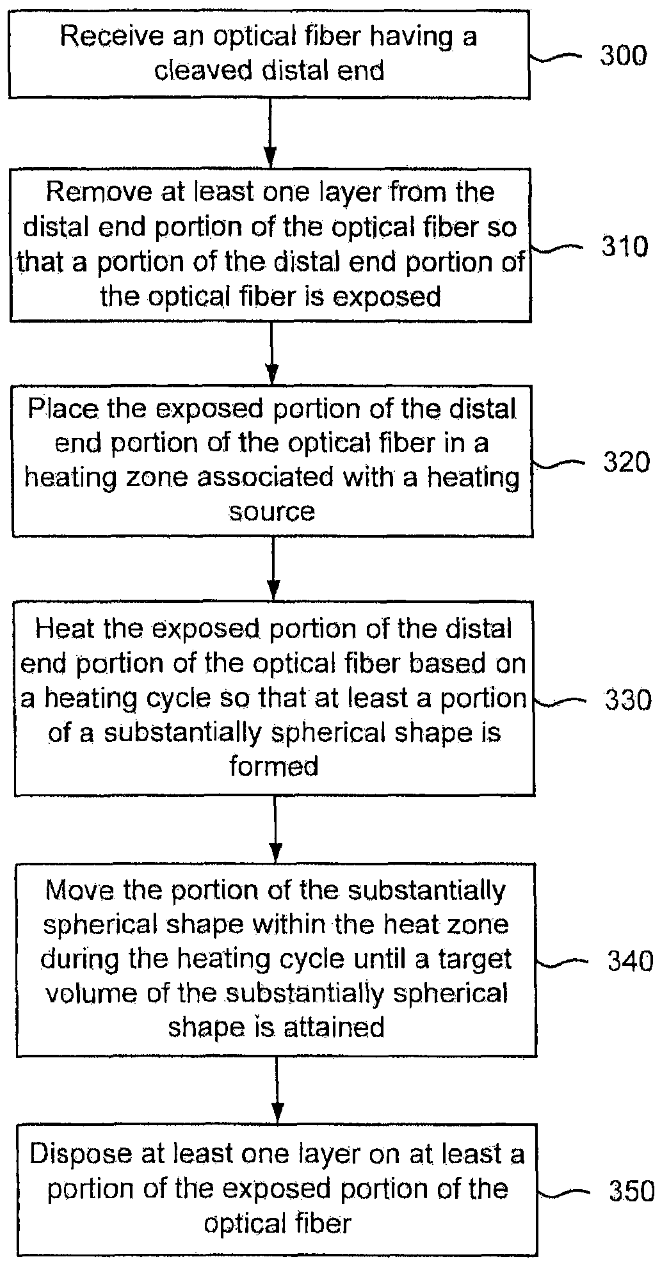
FIG. 3 is a flowchart that illustrates a method for producing a distal end portion of an optical fiber that has a substantially spherical shape, according to an embodiment.

FIG. 3 is a flowchart that illustrates a method for producing a distal end portion of an optical fiber that has a substantially spherical shape, according to an embodiment. An optical fiber having a cleaved distal end is received at 300. The optical fiber can include, for example, a fiber core, one or more cladding layers disposed around the fiber core, one or more buffer layer(s) disposed around the cladding layer(s), and/or one or more jacket layer(s) (disposed around the buffer layer(s)).

At least one layer (e.g., a jacket layer) is removed (e.g., is stripped) from a distal end portion of the optical fiber so that a portion (e.g., a cladding layer) of the distal end portion of the optical fiber is exposed at 310. The layer(s) removed from the distal end portion of the optical fiber can be referred to as removed layer(s). In some embodiments, the distal end can be cleaved after the coating is removed.

The exposed portion of the distal end portion of the optical fiber is placed in a heating zone associated with a heating source at 320. The heating zone can be a heating zone within a fusion splicer. The exposed portion of the distal end portion of the optical fiber is heated based on a heating cycle so that at least a portion of a substantially spherical shape is formed at 330.

The portion of the substantially spherical shape is moved within the heating zone during the heating cycle until a target volume of the substantially spherical shape is attained at 340. A determination as to whether or not the target volume has been attained can be made using, for example, a visual inspection or an optical characteristic associated with the substantially spherical shape at the distal end portion of the optical fiber. More details related to the optical characteristics of the distal end portion of the optical fiber are described in connection with FIGS. 4 through 7. In some embodiments, the heating cycle and the movement of the substantially spherical shaped portion can be defined so that the target volume of the substantially spherical shape is attained.

After the target volume of the substantially spherical shaped portion has been attained, at least one coating can be disposed on at least a portion of the exposed portion of the optical fiber at 350. The layer(s) disposed on the exposed portion of the optical fiber can be referred to as disposed layer(s). The disposed layer(s) can be different than the removed layer(s). The disposed layer(s) can, for example, have different properties (e.g., optical properties) and/or characteristics (e.g., thicknesses) than the removed layer(s).

Figure 4:
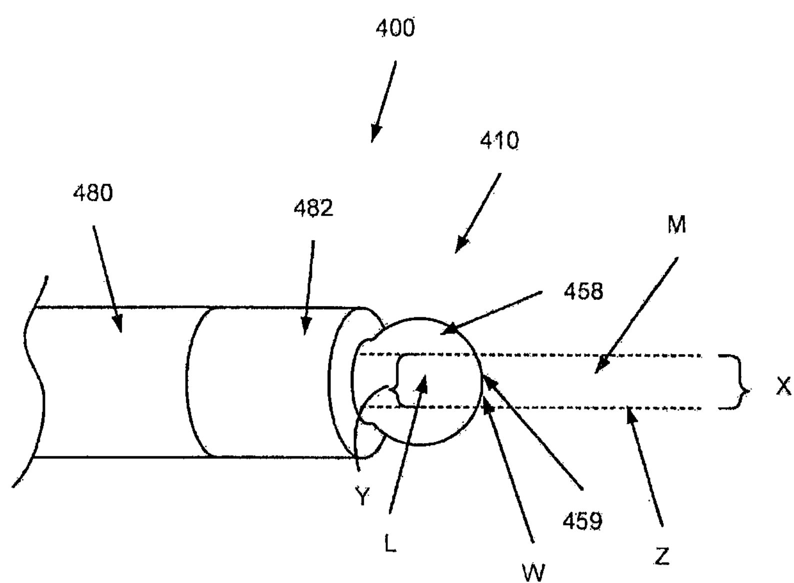
FIG. 4 is a schematic diagram of a perspective view of an optical fiber that has an optical component with a substantially spherical shape, according to an embodiment.

FIG. 4 is a schematic diagram of a perspective view of an optical fiber 400 that has an optical component 458 with a substantially spherical shape, according to an embodiment. The optical component 458 is at a distal end portion 410 of the optical fiber 400. As shown in FIG. 4, the optical fiber 400 has a first segment of coatings 480 and a second segment of coatings 482. The second segment of coatings 482 can be disposed distal to the first segment of coatings 480 and can be disposed after the optical component 458 has been formed.

As shown in FIG. 4, the optical fiber 400 is associated with a beam profile Z that has a width Y within the optical component 458 and a width X outside of the optical component 458. The beam profile Z can also be defined by a collection or bundle of optical paths. Although beam profile Z is shown with parallel lines, it should be understood that the beam profile Z can slightly diverge or converge in a distal direction. Laser energy emitted from for example, a laser energy source can be propagated within the optical fiber 400 and along the beam profile Z. As shown in FIG. 4, the width Y and the width X are substantially equal. In other words, the width of the beam profile Z can be substantially unchanged by an interface W defined by a distal surface 459 of the optical component 458 and a medium (e.g., air, water) outside of the optical component 458 because the distal surface 459 can be relatively flat with respect to beam profile Z.

In some embodiments, a radius of curvature of the surface 459 of the optical component 458 is defined so that a focal length associated with a first portion L of the beam profile Z proximal to the interface W is substantially the same as a focal length associated with a second portion M of the beam profile Z distal to the interface W. In some embodiments, a first focal length associated with the first portion L of the beam profile Z proximal to the interface W can be different than a second focal length associated with the second portion M of the beam profile Z distal to the interface W. The first focal length and the second focal length can be separated, for example, by a specified distance. In some embodiments, a difference between the first focal length and the second focal length is relatively small compared with a desirable operating distance. The operating distance can, be a distance between the distal surface 459 of the optical component 458 and a target object (not shown) when the optical fiber 400 is in use during a medical procedure. In some embodiments, a desirable operating distance can be less than 1 cm. In some embodiments, a focal length of the second portion M of the beam profile Z can be relatively long compared with a desirable operating distance (e.g., greater than 100 times the desirable operating distance). In some embodiments, a radius of curvature of the surface 459 of the optical component 458 can be defined so that the second portion M of the beam profile Z is substantially collimated.

In some embodiments, the size of the optical component 458 (and a radius of curvature of the surface 459 of the optical component 458) can be defined so that the beam profile Z has a substantially constant width or a width that changes a specified amount. For example, a volume of the optical component 458 can be defined so that the distal surface 459 is relatively flat and the beam profile Z can have a width Y that is substantially equal to the width Z over a specified distance. In some embodiments, the distal surface 459 of the optical component 458 can be polished so that it is substantially flat.

Figure 5:
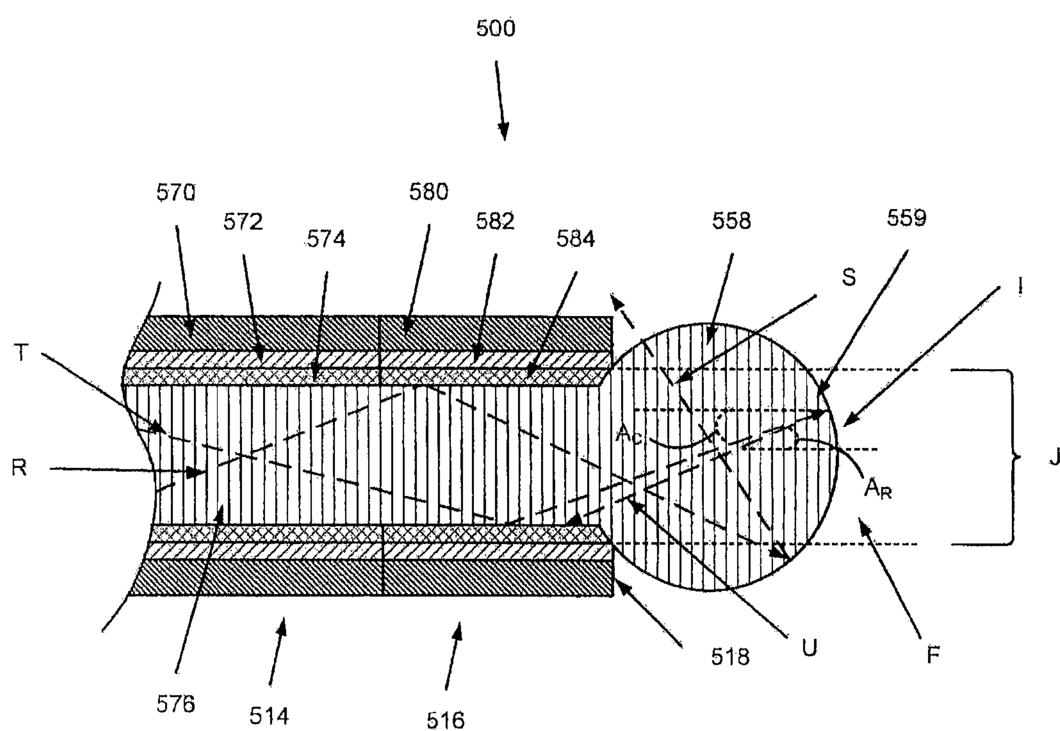
FIG. 5 is a schematic diagram of a side cross-sectional view of an optical fiber that has an optical component with a substantially spherical shape, according to an embodiment.

FIG. 5 is a schematic diagram of a side cross-sectional view of an optical fiber 500 that has an optical component 558 with a substantially spherical shape, according to an embodiment. The optical fiber 500 has a fiber core 576 and two coating segments—coating segment 514 and coating segment 516—that are circumferentially disposed around the fiber core 576. At least a portion of coating segment 516 is disposed between coating segment 514 (distal to the coating segment 514) and the optical component 558. As shown in FIG. 5, at least a portion of coating segment 516 is proximal to a distal end of the optical component 558. In some embodiments, the portion of the coating segment 516 can be in contact with at least a portion of the optical component 558. In some embodiments, coating segment 516 can be disposed around the fiber core 576 after the optical component 558 has been formed.

Coating segment 514 includes a cladding layer 574, a buffer layer 572, and a jacket layer 570, and coating segment 516 similarly includes a cladding layer 584, a buffer layer 582, and a jacket layer 580. One or more portions of coating segment 514 can have different properties than one or more portions of coating segment 516. For example, in some embodiments, an index of refraction and/or a thickness of at least one of the layers associated with coating segment 514 (e.g., the cladding layer 574) can be substantially the same as or different than an index of refraction and/or a thickness of at least one of the layers associated with coating segment 516 (e.g., the cladding layer 584). In some embodiments, a first coating segment disposed between an optical component and a second coating segment can have a number of layers that is different than a number of layers associated with the second coating segment.

As shown in FIG. 5, a portion of laser energy R is propagated along the fiber core 576 toward an interface I, and at least a portion of the laser energy R is back-reflected at the interface I defined by a distal surface 559 of the optical component 558 and a medium (e.g., air) outside of the optical component 558. The back-reflected-laser energy is shown as laser energy S and can be referred to as back-reflected laser energy S. In some embodiments, the laser energy S can be back-reflected laser energy according to Fresnel reflection. As shown in FIG. 5, the back-reflected laser energy S is propagated out of the optical component 558 without impacting any portion (e.g., portion 518) of coating segment 516. In some embodiments, the back-reflected laser energy S can be referred to as back-reflected/escaped laser energy because the laser energy is back-reflected and propagated out of the optical component 558 without impacting any portion of coating segment 516. In some embodiments, a fraction (e.g., less than 10%, more than 10%) of the laser energy R can be back-reflected as laser energy S.

In some embodiments, a volume of the optical component 558 can be defined based on a desirable back-reflection of laser energy (e.g., desirable level of back-reflection, desirable angle of back-reflection). For example, a volume of the optical component 558 can be defined so that some laser energy (such as laser energy R) that is incident on a specified area of the interface I will be back-reflected and propagated out of the optical component 558 (such as laser energy S) without impacting any portion of coating segment 516. Laser energy that impacts a portion of coating segment 516 can cause the portion of coating segment 516 to, for example, burn if the power density levels exceed a threshold level. The volume of the optical component 558 can be defined so that laser energy (such as laser energy T) that is incident on a specified area of the interface I will be back-reflected (shown as laser energy U) without propagating out of the optical component 558 (and/or without propagating into one or more of the layers associated with coating segment 516). In some embodiments, the volume of the optical component 558 can be defined so that a specified portion (e.g., a specified percentage) of laser energy propagated in a distal direction within the optical fiber 500 will be back-reflected (at the interface I) without propagating out of the optical component 558 (and/or without propagating into one or more of the layers associated with coating segment 516).

An angle between a longitudinal axis of the fiber core 576 and the direction of laser energy propagating toward the interface I can be referred to as a critical angle. The critical angle of laser energy T is shown in FIG. 5 as critical angle Ac-An angle between a longitudinal axis of the fiber core 576 and the direction of back-reflected laser energy can be referred to as an angle of reflectance. The angle of reflectance of laser energy U is shown in FIG. 5 as angle of reflectance $A_R$. Although not shown, in some embodiments, an angle between an axis normal to the interface I where laser energy is incident and the direction of that laser energy propagating toward the interface I can be referred to as an angle of incidence. In some embodiments, a volume of the optical component 558 can be defined so that all (or a specified portion of) laser energy propagating toward interface I and having a specified range of critical angles (e.g., a range of critical angles between 20° and 50°) will be back-reflected/escaped laser energy and/or laser energy back-reflected into the fiber core 576 without impacting (and/or burning) segment 516 in an undesirable fashion. In some embodiments, a volume of the optical component 558 can be defined so that all (or a specified portion of) back-reflected laser energy (such as laser energy U) having a specified range of angles of reflectance (e.g., a range of angles of reflectance between 20° and 50°) will not impact (and/or burn) the segment 516 in an undesirable fashion.

In some embodiments, a volume of the optical component 558 can be defined so that a ratio of laser energy that is back-reflected/escaped (such as back-reflected laser energy S) and laser energy that is back-reflected into the fiber core 576 (such as back-reflected laser energy U) will be at (e.g., approximately at), above, or below a specified value. In some embodiments, a volume of the optical component 558 can be defined so that a ratio of laser energy that is back-reflected/escaped (such as back-reflected laser energy S) and laser energy that is back-reflected and impacts a portion of the segment 516 in an undesirable fashion will be at (e.g., approximately at), above, or below a specified value. In some embodiments, a volume of the optical component 558 can be defined so that a ratio of laser energy that is back-reflected into the fiber core 576 (such as back-reflected laser energy U) and laser energy that is back-reflected and impacts a portion of the segment 516 in an undesirable fashion will be at (e.g., approximately at), above, or below a specified value.

In some embodiments, a volume of the optical component 558 can be defined so that one or more characteristics of the interface I will be substantially the same as a straight-cut (e.g., cleaved) end of an optical fiber (not shown). Specifically, the volume of the optical component 558 can be defined so that laser energy back-reflected at the interface I is reflected in a fashion (e.g., at angles, with a back-reflected numerical aperture) that is substantially similar to laser energy back-reflected from, for example, an fiber-air interface of a straight-cut fiber.

In some embodiments, the volume of the optical component 558 can be defined so that a beam profile F of laser energy propagated through the optical fiber 500 and out of the optical component 558 of the optical fiber 500 will be substantially unchanged proximal to the interface I (within the optical fiber 500) and distal to the interface I (outside of the optical fiber 500) as shown in FIG. 5. In other words, the beam profile F can have a width J that is substantially the same distal to the interface I and proximal to the interface I. In some embodiments, a volume of an optical component can be defined so that an outer diameter of the optical component is greater than an outer diameter of one or more coating segments around an optical fiber.

Figure 6:
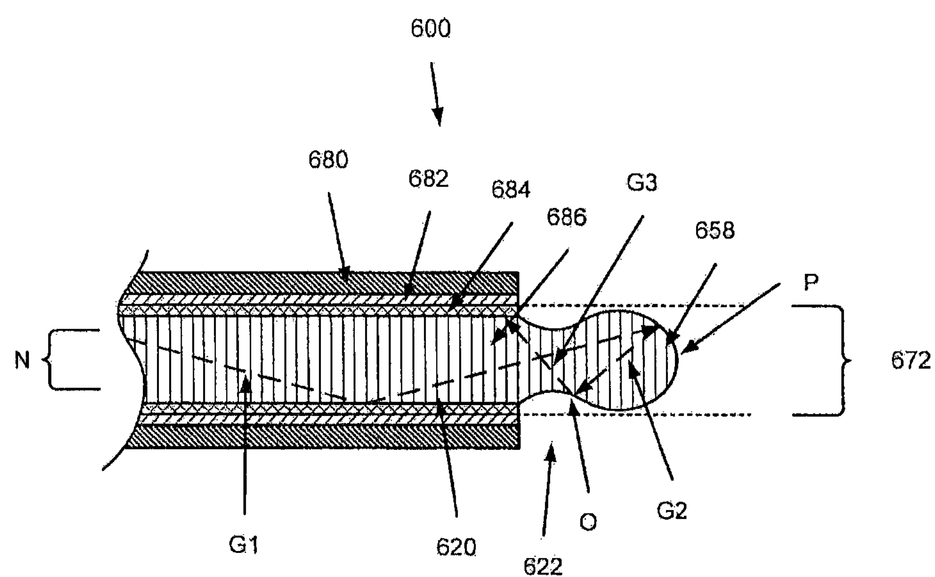
FIG. 6 is a schematic diagram of a side cross-sectional view of an optical fiber that has an optical component with a substantially spherical shape, according to an embodiment.

FIG. 6 is a schematic diagram of a side cross-sectional view of an optical fiber 600 that has an optical component 658 with a substantially spherical shape, according to an embodiment. The optical fiber 600 has a jacket layer 680, a buffer layer 682, a cladding layer 684, and a fiber core 686. As shown in FIG. 6, laser energy G1 is propagated along the fiber core 686 and back-reflected at an interface P defined by a distal surface of the optical component 658 and a medium (e.g., air) outside of the optical component 658. The back-reflected laser energy is shown as laser energy G2 (can be referred to as back-reflected laser energy G2).

The fiber core 686 has a recessed axial portion 622 that is disposed between a axial portion 620 of the fiber core 686 (also can be referred to as a straight axial portion 620) and the optical component 658. The recessed axial portion 622 of the fiber core 686 has an outer diameter N that is less than an outer diameter of the axial portion 620 of the fiber core 686, which is proximal to the recessed axial portion 622 of the fiber core 686. Specifically, the recessed axial portion 622 of the fiber core 686 has a curved, concave shape that defines a portion of an interface O where the laser energy G2 is reflected as laser energy G3. The recessed axial portion 622 is defined to redirect the laser energy G2 as laser energy G3 so that the laser energy G2 may not propagate out of the fiber core 686 and/or impact, for example, the jacket layer 680, the buffer layer 682, and/or the cladding layer 684.

In some embodiments, the recessed axial portion 622 of the fiber core 686 can have a different shape than that shown in FIG. 6. For example, the recessed axial portion 622 of the fiber core 686 can have one or more flat portions (e.g., flat side walls) and/or one or more convex portions (e.g., one or more protrusions). In some embodiments, a fiber core of an optical fiber can have an axial portion that protrudes from the fiber core (rather than being recessed). The axial portion can be configured to redirect laser energy that has been back-reflected at an interface at a distal end of an optical component.

In some embodiments, the recessed axial portion 622 of the fiber core 686 can be formed using a mechanical machining and/or chemical etching process. For example, the fiber core 686 can be polished until the recessed axial portion 622 of the fiber core 686 is formed. In some embodiments, the recessed axial portion 622 can be formed using a heating and pulling process. For example, a portion of the fiber core 686 proximal to the optical component 658 can be heated using a heating element and the optical component 658 can be pulled in a distal direction until the recessed axial portion 622, of the fiber core 686 is formed.

Although not shown, in some embodiments, the recessed axial portion 622 of the fiber core 686 can have a jacket layer, a buffer layer, and/or a cladding layer. The jacket layer, the buffer layer, and/or the cladding layer can be disposed over the recessed axial portion 622 after the recessed axial portion 622 of the fiber core 686 has been formed. In some embodiments, a recessed axial portion can be formed from at least a portion of a fiber core of an optical fiber and/or a different portion of the optical fiber such as, for example, a cladding layer of the optical fiber. In such embodiments, the recessed axial portion can have a composition that is a mixture of the fiber core and the cladding layer.

Figure 7:
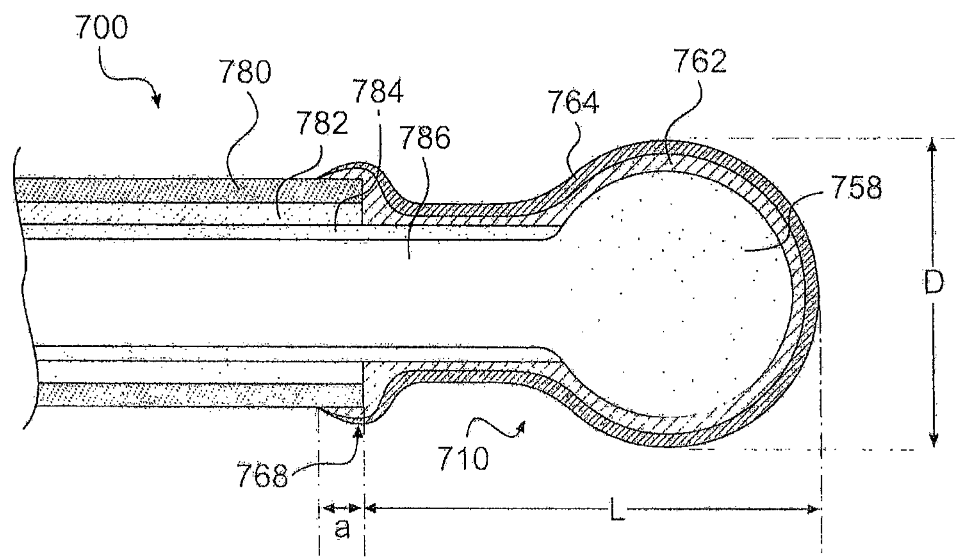
FIG. 7 is a schematic diagram of a side cross-sectional view of an optical fiber that has an optical component with a substantially spherical shape, according to an embodiment.

FIG. 7 is a schematic diagram of a side cross-sectional view of an optical fiber 700 that has an optical component 758 with a substantially spherical shape, according to another embodiment. As in some of the previous embodiments, the optical fiber 700 includes a jacket layer 780 and a buffer layer 782 that have been cleaved to expose a cladding layer 784 circumferentially disposed about a fiber core 786. The optical component 758 of a substantially spherical shape may be formed at the distal end of the cleaved optical fiber 700 by melting the cladding layer 784 and the fiber core 786 at a distal portion of the optical fiber 700. The optical component 758 may be formed by melting a portion of the optical fiber 700 and allowing surface tension to pull the molten material into a substantially spherical shape. A process described with reference to FIGS. 2A-2E, or a different process may be used to form the optical component 758. In some embodiments, an exposed portion 710 of the optical fiber 700 outside the jacket 780 may have a length L between about 3 mm and about 7 mm. In some embodiments, one or more coatings may be applied on the exposed portion 710. These coatings may protect the optical fiber 700 from moisture which may cause embrittlement of the optical fiber 700.

In some embodiments, two coatings may be applied to the surface of the exposed portion 710. These two coatings may include a first coating 762 and a second coating 764. These coatings may be made of a polymeric or acrylic materials. In some embodiments, materials such as an EFIRON® polymer clad resin (for example, EFIRON® PC-370) and Klear shield 2-2002 may be used as the coating materials. In some embodiments, EFIRON® PC-370 may be used as the inner coating and the Klear shield material may be used as the outer coating, while in other embodiments, their order may be reversed. In some embodiments, other polymeric materials may be used as the coating materials.

The first coating 762 and second coating 764 may cover substantially the entire surface of the exposed portion 710 including the optical component 758. In some embodiments, these coatings may overlap with the cleaved distal portion of the jacket layer 780 to form an overlapping region 768. Although this overlapping region 768 may have any length in general, in some embodiments, the length a of the overlapping region may be between about 1 mm and about 5 mm. Although an optical fiber 700 with two coatings is depicted in FIG. 7, this is only exemplary, and other embodiments may have a different number of coatings. For instance, in some embodiments, only one coating (such as, for example, one of first coating 762 or second coating 764) may be present, while in other embodiments more than two coatings may be present.

The first coating 762 and the second coating 764 may be formed on optical fiber 700 by successively dipping the distal portion of the optical fiber 700 into the coating materials and then curing the coated optical fiber. To form first coating 762, in some embodiments, a coating material (such as, for example, Efiron polymer clad PC-370) may be heated to between about 50° C. and 60° C. The distal portion of the optical fiber 700 may be dipped into the coating material at a rate of, for example, about 0.25 in/sec. The coated optical fiber 700 may then be withdrawn from the coating material at, for example, a rate of about 0.25 in/sec. The coated optical fiber 700 may further be cured to harden the coating. The coating may be cured by using ultra-violet light (having a wavelength of, for example, about 250 nm or less) or by any other known technique. To form a second coating 764 over the first coating 762, a similar or a different process may be used. It should be emphasized that the described method of forming the coating is only exemplary, and in some embodiments, a different process may be followed.

Figure 8:
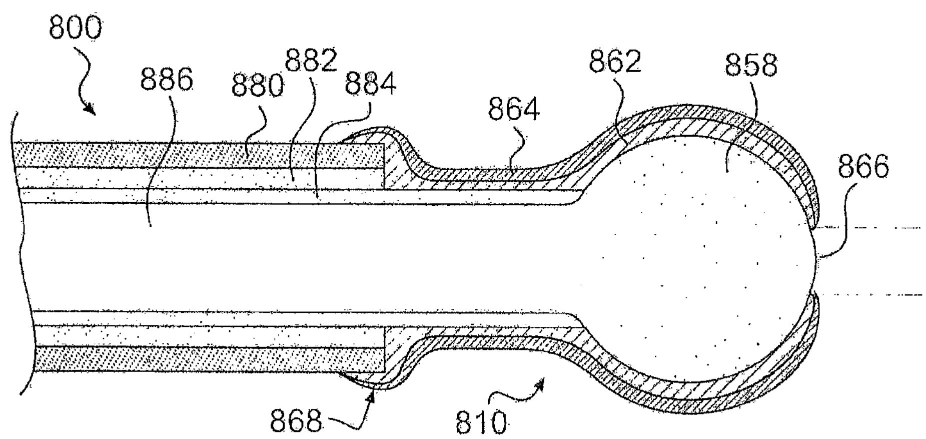
FIG. 8 is a schematic diagram of a side cross-sectional view of an optical fiber that has an optical component with a substantially spherical shape, according to an embodiment.

FIG. 8 is a schematic diagram of a side cross-sectional view of an optical fiber 800 that has an optical component 858 with a substantially spherical shape, according to another embodiment. The optical fiber 800 of FIG. 8 may be similar to the optical fiber 700 of FIG. 7, and may include a substantially spherical optical component 858 at the distal end. Optical fiber 800 may also include a jacket layer 880 and a buffer layer 882 cleaved to expose an exposed portion 810 with a cladding layer 884 disposed around fiber core 886. As in the embodiment of FIG. 7, the optical component 858 of FIG. 8 may also be formed by melting a portion of the cladding layer 884 and the fiber core 886 at the distal end. The optical fiber 800 of FIG. 8 may also include a first coating 862 and a second coating 864 coated over regions of the exposed portion 810 of the optical fiber 800 to form an overlapping region 868 at the distal end of the jacket layer 880. A portion of the external surface, such as, for example, a distal tip portion 866, of the optical component 858 may be exposed through the first coating 862 and the second coating 864. In some embodiments, this distal tip portion 866 may have a substantially circular shape. In some embodiments, the substantially circular tip portion 866 may have substantially the same diameter as the fiber core 886 (or the combined diameter of the cladding layer 884 and the fiber core 886). Although the distal tip portion 866 may be formed in any manner, in some embodiments, after the first coating 862 and second coating 864 are formed, a laser may be fired though the optical fiber 800 to burn off the coatings at the distal tip portion 866.

While various embodiments have been described above, it should be understood that they have been presented by way of example only, and not limitation. For example, the optical fiber described herein can include various combinations and/or sub-combinations of the components and/or features of the different embodiments described. Although described with reference to use for treatment of kidney stones and/or symptoms related to BPH, it should be understood that the optical fiber, as well as the methods of using the optical fiber can be used in the treatment of other medical conditions. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. An apparatus, comprising:
- an optical fiber having a proximal end and a distal end having a substantially spherically-shaped portion;
- a cladding layer circumferentially disposed about the optical fiber;
- a first coating segment circumferentially disposed on a first length of the cladding layer; and
- a second coating segment having a first portion circumferentially disposed on a second length of the cladding layer and having a second portion circumferentially disposed on at least a portion of the first coating segment to form an overlapped region, wherein the first portion of the second coating segment extends distally of a distal end of the first coating segment to a distal-most end of the substantially spherically-shaped portion.

2. The apparatus of claim 1, wherein the overlapped region has a length between 1 and 5 mm.

3. The apparatus of claim 1, wherein the second coating segment includes a second inner coating and a second outer coating, wherein the second inner coating is positioned radially inwards of the second outer coating.

4. The apparatus of claim 3, wherein each of the second inner coating and second outer coating includes at least one of an acrylic or a polymer.

5. The apparatus of claim 1, wherein the first coating segment terminates between 3 and 7 mm from a distal-most end of the optical fiber.

6. The apparatus of claim 1, wherein the first coating segment includes a jacket layer and a buffer layer.

7. The apparatus of claim 1, wherein an index of refraction of the first coating segment is different from the index of refraction of the second coating segment.

8. The apparatus of claim 1, wherein the optical fiber includes a core integral with the substantially spherically-shaped portion.

9. The apparatus of claim 8, wherein a radius of curvature of a surface of the substantially spherically-shaped portion is such that a cross-sectional dimension of a beam of energy propagated through the core is different than a cross-sectional dimension of a beam of energy emitted through the surface and distally of the substantially spherically-shaped portion.

10. An apparatus, comprising:
- an optical fiber having a proximal end and a distal end having a substantially spherically-shaped portion, the optical fiber including a cladding layer circumferentially disposed about a core;
- a first coating segment circumferentially disposed along a first length of the cladding layer; and
- a second coating segment having a first portion circumferentially disposed along a second length of the cladding layer, wherein the first portion of the second coating segment extends distally of a distal end of the first coating segment to fully cover the substantially spherically-shaped portion, the second coating segment having a second portion;

wherein a radius of curvature of a surface of the substantially spherically-shaped portion is such that a cross-sectional dimension of a beam of energy propagated through the core is the same as a cross-sectional dimension of a beam of energy emitted through the surface and distally of the substantially spherically-shaped portion.

11. The apparatus of claim 10, wherein an index of refraction of the first coating segment is different from the index of refraction of the second coating segment.

12. The apparatus of claim 10, wherein the core is integral with the substantially spherically-shaped portion.

13. The apparatus of claim 10, wherein the second coating segment includes a second inner coating and a second outer coating, wherein the second inner coating is positioned radially inwards of the second outer coating.

14. The apparatus of claim 13, wherein each of the second inner coating and second outer coating includes at least one of an acrylic or a polymer.

15. An apparatus, comprising:

an optical fiber having a proximal end and a distal end having a substantially spherically-shaped portion having a largest diameter extending perpendicular to a longitudinal axis of the optical fiber, the optical fiber including a cladding layer circumferentially disposed about a core;

a first coating segment circumferentially disposed along a first length of the cladding layer; and a second coating segment having a first portion circumferentially disposed along a second length of the cladding layer, wherein the second coating segment extends distally of a distal end of the first coating segment to a location distal of the diameter and to the distal-most end of the substantially spherically-shaped portion.

16. The apparatus of claim 15, wherein an index of refraction of the first coating segment is different from the index of refraction of the second coating segment.

17. The apparatus of claim 15, wherein the core is integral with the substantially spherically-shaped portion.

18. The apparatus of claim 15, wherein the diameter of the substantially spherically-shaped portion is larger than a diameter of the cladding layer.

19. The apparatus of claim 15, wherein the second coating segment includes a second inner coating and a second outer coating, wherein the second inner coating is positioned radially inwards of the second outer coating.

20. The apparatus of claim 19, wherein each of the second inner coating and second outer coating includes at least one of an acrylic or a polymer.

* * * * *